United States Patent
Bernareggi et al.

(10) Patent No.: US 10,646,586 B2
(45) Date of Patent: May 12, 2020

(54) AQUEOUS ORAL SOLUTIONS OF STEROID HORMONES AND HYDROXYPROPYL-BETA-CYCLODEXTRIN WITH OPTIMISED BIOAVAILABILITY

(71) Applicant: ALTERGON S.A., Lugano (CH)

(72) Inventors: Alberto Bernareggi, Lugano (CH); Nadia Puppini, Lugano (CH); Alessandro Nencioni, Lugano (CH)

(73) Assignee: ALTERGON S.A., Lugano (CH)

( * ) Notice: Subject to any disclaimer, the term of this patent is extended or adjusted under 35 U.S.C. 154(b) by 86 days.

(21) Appl. No.: 14/647,570

(22) PCT Filed: Nov. 22, 2013

(86) PCT No.: PCT/EP2013/003538
§ 371 (c)(1),
(2) Date: May 27, 2015

(87) PCT Pub. No.: WO2014/082724
PCT Pub. Date: Jun. 5, 2014

(65) Prior Publication Data
US 2015/0297752 A1 Oct. 22, 2015

(30) Foreign Application Priority Data
Nov. 28, 2012 (IT) ............... MI2012A2027

(51) Int. Cl.
| A61K 47/48 | (2006.01) |
| A61K 31/57 | (2006.01) |
| A61K 31/568 | (2006.01) |
| A61K 47/69 | (2017.01) |
| B82Y 5/00 | (2011.01) |

(52) U.S. Cl.
CPC ........ A61K 47/6951 (2017.08); A61K 31/568 (2013.01); A61K 31/57 (2013.01); B82Y 5/00 (2013.01)

(58) Field of Classification Search
CPC .............. A61K 47/48969; A61K 31/57; A61K 31/568; B82Y 5/00
USPC .......................................................... 514/58
See application file for complete search history.

(56) References Cited

U.S. PATENT DOCUMENTS

| 4,596,795 A | 6/1986 | Pitha | |
| 4,727,064 A * | 2/1988 | Pitha | A61K 31/565 |
| | | | 106/205.01 |
| 5,024,998 A * | 6/1991 | Bodor | A61K 31/43 |
| | | | 424/1.85 |
| 7,029,657 B2 * | 4/2006 | Pike | A61K 31/56 |
| | | | 424/426 |
| 2006/0008420 A1 | 1/2006 | Daniels | |
| 2006/0058262 A1 | 3/2006 | Zoppetti | |
| 2010/0240631 A1 | 9/2010 | Bellorini et al. | |

OTHER PUBLICATIONS

Margo et al, Am. Fam. Physician, 2006, 73, 1591-98.*
Dahan et al, J. Pharm. Sci. 2010, 99(6), 2739-2749.*
Sweetman, Martindale: The Complete Drug Reference, 2002, 1452-65 and 1488-91.*
Brewster, Journal of Parenteral Science and Technology, 1989, 43(5), 231-240.*
Szente, Advanced Drug Delivery Reviews, 1999, 36, 17-28.*
Zoppetti, G., et al., Water Soluble Progesterone-Hydroxypropyl..., Journal of Inclusion Phenomena and Macrocyclic chemistry..., vol. 57, No. 1-4, pp. 283-288, 2007.
Fini, Adamo, et al., ATR/Raman and Fractal Characterization of HPBCD/Progesterone..., Pharmaceutical Research, vol. 25, No. 9, pp. 2030-2040, 2008.
Dahan, Arik, et al., The Solubility-Permeability Interplay in Using Cyclodextrins..., Journal of Pharmaceutical Sciences, vol. 99, No. 6, pp. 2739-2749, 2010.
Pitha, J., et al., Effects of Ethanol on Formation of Inclusion Complexes of Hydroxypropylcyclodestrins..., International Journal of Pharmaceutics, vol. 80, No. 1-3, pp. 243-251, 1992.
Szente, Lajos, et al., Highly Soluble Cyclodextrin Derivatives: Chemistry..., Advanced Drug Delivery Reviews, vol. 36, pp. 17-28, 1999.
Beta-Hydroxypropyl-Cyclodextrin (Encapsin (TM) Replacement) Available through RDI Divison, Internet Citation, 2004.
International Search Report issued in PCT Application No. PCT/EP2013/003538.
Prometrium Product Information, SCH 961 Capsules 100 MG, HRT, pp. 1.
Andriol Technical Data Sheet and Prescription, 2018, pp. 1-15.

* cited by examiner

*Primary Examiner* — Ganapathy Krishnan
(74) *Attorney, Agent, or Firm* — Lucas & Mercanti, LLP

(57) ABSTRACT

The present invention concerns the preparation and the therapeutic use of aqueous solutions of Progesterone or Testosterone, complexed with hydroxypropyl-3-cyclodextrin (HPβCD) that are suitable for oral administration. The solutions are characterised by a specific molar ratio between HPβCD and the hormones such as to ensure high hormone plasma levels, following oral administration, thanks to the optimisation of their solubility, permeability, metabolic stability and ultimately, bio availability. The formulation object of the present patent makes it possible to achieve effective plasma concentrations following oral administration of lower doses of hormone with respect to oral formulations currently on the market (e.g. Prometrium, Andriol) to the advantage of greater safety and compliance of the patients.

14 Claims, 10 Drawing Sheets

AQUEOUS ORAL SOLUTIONS OF STEROID HORMONES AND HYDROXYPROPYL-BETA-CYCLODEXTRIN WITH OPTIMISED BIOAVAILABILITY

TECHNICAL FIELD

The present invention concerns the field of oral formulations of steroid hormones. Aqueous solutions are described, which have been specifically studied for the oral administration of Progesterone or Testosterone, comprising said hormones complexed with specific cyclodextrin derivatives with a high degree of purity.

STATE OF THE ART

Progesterone is a steroid hormone produced by the ovaries (in the corpus luteum after ovulation), by the adrenal glands and by the placenta during pregnancy. In women, the levels of Progesterone are relatively low in the first half of the menstrual cycle (pre-ovulation phase), increasing after ovulation and are kept high thanks to the corpus luteum during the second stage of the cycle called luteal or progesterone phase.

High hematic Progesterone levels allow the creation of conditions suitable for the insemination of the egg cell and its nesting inside the endometrium, such events signalling the beginning of the pregnancy. During gestation, Progesterone seems to diminish the maternal immune response allowing the body to accept the pregnancy. The normal fall of Progesterone levels after delivery triggers the production of milk. If a pregnancy does not occur, the Progesterone levels diminish leading to menstruation. If the ovulation does not occur and the corpus luteum does not develop, the Progesterone levels can be low and lead to dysfunctional uterine bleeding. Women in menopause have Progesterone levels that are relatively low, whereas adult men have levels of such a hormone that are similar to those of women during the follicular phase of the menstrual cycle.

Concerning reproduction, during insemination, Progesterone influences the migration of sperm through the female genital ducts.

At a therapeutic level, Progesterone is used for treating different pathologies such as for example endometrial hyperplasia, premenstrual syndrome, treatment of the symptoms of menopause and, in the case of female infertility, it can be administered in the protocols of artificial insemination when it is necessary for there to be a support of the luteal phase.

Testosterone is an androgenic steroid hormone that is mainly produced by the Leydig cells of the testicle and, in a minor portion, by the adrenal cortex. It is also present in women, as an intermediate product of the synthesis of oestrogen. In men it has the function of developing the sex organs (differentiation of the testicles and of all the genital apparatus) and the secondary sexual characteristics, like the beard, the distribution of body hair, the tone of the voice and the musculature. Testosterone, during puberty, also acts on the development of the skeleton, limiting the stretching of the long bones and, in such a way, preventing an excessive growth of the limbs.

In adult men, Testosterone levels have a fundamental role in fertility, vitality and health (especially intended as protection from metabolic diseases like hypertension and diabetes mellitus). Testosterone contributes towards ensuring fertility since it acts on the maturation of the spermatozoa in the testicles. It influences both the quality and the quantity of sperm produced, also operating on the seminal ducts and on the prostate. Testosterone also regulates desire, erection and sexual satisfaction, synchronising sexual desire with the actual sex act, regulating the beginning and the end of the erection of the penis. A deficit of libido (sexual desire) is often associated with a Testosterone dysfunction. This has also been highlighted for the female sexual desire following its diminishing in the postmenopausal period. Testosterone is used pharmacologically in both men and women, if there are alterations in its levels.

In the therapeutic field, Testosterone is used for treating different pathologies like, for example, treating hypoactive sexual desire disorder and for treating male hypogonadism, both primary and secondary.

Both the hormones belong to class II of the BCS classification having low solubility and high permeability. Their reduced oral bioavailability is caused by the following concurrent factors: a very low aqueous solubility that conditions the speed and the amount of absorption through the intestinal barrier, a significant presystemic metabolism in the gastrointestinal tract, the hepatic first-pass effect. The necessity of reaching suitable plasma levels makes it preferable, for both hormones, to be administered in a way that completely or partially excludes the gastrointestinal tract, i.e. parenteral, vaginal, rectal, sublingual and buccal. It is necessary to underline, however, that oral administration is the option that is preferred by the patient with respect to the other ways mentioned, especially if the treatment is long term. The improvement of the oral bioavailability of steroid hormones is therefore currently the subject of advanced formulation research.

In oral formulations containing Progesterone on the market, the problem of low aqueous solubility of the hormone, together with gastrointestinal and hepatic presystemic metabolism, leads to reduced plasma levels with respect to the other administration methods like for example the buccal/sublingual method; for example, the Martindale (Thirty-second edition—1999) "The complete drug reference", page 1460, indicates that Progesterone has a short elimination half-life and undergoes extensive first-pass hepatic metabolism when given by mouth; oral bioavailability is very low although it may be increased somewhat by administration in an oily vehicle and by micronisation; cf. also *Curr. Opin. Investig. Drugs*. 2003 October; 4(10):1213-9, reporting that oral delivery of testosterone is not possible due to rapid first pass metabolism and short half-life. The problem of the poor solubility in some cases was tackled by dispersing the micronized powder of the hormone in the oil phase (example: Prometrium). However, clinical pharmacokinetic studies highlight that the administration of such a formulation, as shall be described in greater detail in the rest of the description, ensures plasma levels of progesterone that are substantially lower than those obtained with the formulation object of the present invention.

In the case of Testosterone, on the other hand, an oral formulation in soft capsules of Testosterone undecanoate is available on the market. The ester, absorbed and transported into the systemic circulation through the intestinal lymphatic system, ensures a modest systemic exposure, while avoiding the hepatic first-pass metabolism. This formulation moreover leads to the chemical modification of the hormone and makes the esterified molecule circulate, which requires being hydrolysed so as to be able to restore the pharmacologically active form of the hormone.

Complexation with cyclodextrins is generally used to improve the solubility of active substances that are not very soluble. Cyclodextrins (CD) are produced starting from starch and comprise a family of cyclic oligosaccharides formed by 6, 7 or 8 monomers of D-(+)glucopyranose joined to one another with an α,1-4 glucosidic bond and closed in a ring. Three-dimensionally, cyclodextrins have a hollow truncated cone-shape structure and based upon the number of monomers: 6, 7, or 8 they are called alpha (αCD), beta (βCD) or gamma CD (γCD). The three CD classes differ from one another for the size of the ring and therefore of the cavity. The hydroxyl groups are arranged on the outer edges, whereas in the cavity there are only atoms of hydrogen and oxygen bridges. This ensures that the central cavity has a hydrophobic nature, whereas the outer part characterised by the presence of hydroxyl groups has high hydrophilicity. Their particular structure makes it possible to receive hydrophobic molecules inside the cavity making them soluble in water. The solubility of the CD has been further improved through chemical modifications in position 2, 3 and 6 of the hydroxyl groups giving alkyl-ethers or introducing new functional groups. Amongst the chemically modified cyclodextrins there is hydroxypropyl-β-cyclodextrin (HPβCD) which is widely used in the pharmaceutical field.

Complexation with cyclodextrin has also been used for improving the solubility of the steroid hormones. Patent US2006/0058262, to the same Applicant, and Zoppetti et al, *J. Incl. Phenom. Macrocycl. Chem.*, 2007, 57, p. 283-288 propose injectable formulations of progesterone, starting from the consideration that suitable plasma levels of progesterone cannot be achieved orally; the highly stable injectable formulations proposed in these references comprise a complex of Progesterone (Prg) with hydroxypropyl-β-cyclodextrin (HPβCD) containing an amount of unsubstituted β-cyclodextrin below 0.1% p/p; the parenteral administration makes it possible to obtain suitable plasma levels in a short time avoiding the hepatic first-pass effect. The review article Szente et al. Advanced Drug Delivery Reviews, 36, 199, p. 17-28 mentions the challenges of purifying HPβCD and states that the amount of non substituted βCD in HPβCD should be less than 0.1%; it additionally refers to two commercial HPβCD products (Encapsin® and Moleculsol®), also described on the web.

U.S. Pat. Nos. 4,727,064 and 4,596,795 to Pitha et al., the patent application US2010/0240631 A1 to the same Applicant, the patent application US 2006/0008420 claim compositions comprising inclusion complexes between steroid hormones with cyclodextrin, through buccal, sublingual or nasal administration: these administration methods, characterised by a rapid absorption into the circulation and without the drawback of the hepatic first-pass, lead to achieving suitable hormone plasma concentrations: for example, based upon U.S. Pat. No. 4,596,795, it is estimated that the ($C_{max}$) for a sublingual dose of 100 mg is of around 50 ng/mL; U.S. Pat. No. 4,596,795 informs that the combinations of the same hormones with hydroxypropyl-β-cyclodextrin administered orally are not active since this administration method exposes the drug to rapid hepatic inactivation; it also indicates that the effective absorption from the oral cavity is dependent on a barrier-free transfer from the solution to the oral tissue The publication Fini et al. *Pharmaceutical Research*, 25(9), 2008, p. 2030-2040, provides ATR Raman and fractal characterization of HPβCD/Progesterone solid particles; the publication Pitha et al. *International Journal of Pharmaceutics*, 80, 1992, p. 243-251, discloses the effect of ethanol on the formation of HPβCD/Testosterone complexes; in both these references a 2/1 ratio of HPβCD/hormone was used to obtain solubilisation of the steroid drug.

It is moreover known that the formation of complexes with cyclodextrin, despite improving the solubility of drugs that are not very soluble, does not per se ensure a high absorption into the circulation; in fact, despite their solubility, these complexes are substantially not absorbed by the gastrointestinal mucous: for example hydroxypropyl-β-cyclodextrin administered orally is only absorbed for about 5% (Gould et al., *Food Chem. Toxicol.* 43(2005) 1451-1459). The publication of Habon et al., *Pharmazie* 39, (1984) H.12, pag. 830-834), discloses that the transmucosal absorption of the drug complexed with cyclodextrin requires a decomplexing step, through which the drug is available for absorption; in particular, the greater the stability of the complex with cyclodextrin (high constant of formation of the complex), the lower the decomplexing rate and therefore the rate at which the drug is made available for absorption. The complexation kinetics between HPβCD and steroid hormones was studied in the above cited publication of Zoppetti et al., 2007: the publication, in particular, describes the complex HPβCD:Prg 2:1 with high formation constant $K_{2:1}=111473.7$ m$^{-1}$, i.e. very stable, and the complex HPβCD:Prg 1:1 with lower formation constant $K_{1:1}=3478.0$ m$^{-1}$, therefore much more easily dissociated.

Also the relative quantity of cyclodextrin with respect to the hormone acts as a factor that limits absorption, as highlighted in the publication by Dahan A. et al. "The Solubility-Permeability Interplay in Using Cyclodextrins as Pharmaceutical Solubilizers: Mechanistic Modeling and Application to Progesterone", *J. Pharm. Sci.*, 99, 6, (2010); the publication relates the rate of the in vivo intestinal permeation of rats and the in vitro simulation in 2 models, PAMPA and Caco-2, of the complex HPβCD and Prg as the concentration of HPβCD increases. From such a study it results that when the concentration of HPβCD increases there is a decrease in the permeation of Progesterone.

In summary, up to present, the efforts to enhance the solubility of progesterone/testosterone (to detriment of permeation) were limited to administration routes involving highly permeable barriers (like the sublingual/buccal route) no barriers at all (parenteral route), and all avoiding the hepatic first pass inactivation; whereas for administration routes characterized by more complex absorption issues and subjected to the hepatic first pass metabolism, in particular the oral route, no efficient solution was envisioned.

The present invention responds to the necessity, so far largely unsatisfied, of new formulations of steroid hormones that are suitable for oral administration, liked by patients, which are highly bioavailable, in particular having high solubility, high absorption at a gastrointestinal level and a reduced presystemic metabolism of the administered hormone.

SUMMARY OF THE INVENTION

The object of the invention are pharmaceutical compositions for use in oral administration of Progesterone or Testosterone, wherein said hormones are complexed, in particular ranges of molar ratios, with a hydroxypropyl-β-cyclodextrin having a certain degree of purity. The Applicant has indeed surprisingly found that the aforementioned steroid hormones, when complexed within the following molar ratios:

a) (HPβCD:Progesterone): comprised between 1.7:1 and 2.4:1, or b) (HPβCD:Testosterone): comprised between 1.7:1 and 3.0:1, and in which said HPβCD contains less than 0.3% of unsubstituted β-cyclodextrin, create aqueous solutions that are particularly suitable for oral administration of said steroid hormones, characterised by an excellent absorption into the circulation and a high hematic concentration of the hormone in the active form. In particular the complexes of the invention, although being less prone to release the hormones in form free for permeation (as compared to the complexes with 1:1 HPBCD:hormone ratio, cf *J Incl Phenom Macrocyl Chem.* 2007-57:283-288), were found unexpectedly active in promoting the transmembrane absorption of progesterone/testosterone. Moreover, they exerted an unexpected protection against hepatic metabolism. The synergy of these effects, allows a highly effective treatment by these hormones, administered via the oral route. Oral bioavalability studies conducted by the inventors show that the present oral formulations result in progesterone/testosterone plasma concentrations comparable to those obtained by buccal administration and markedly higher with respect to those achieved after oral administration of hormone formulations (e.g., progesterone formulation Prometrium®) or hormone prodrugs (e.g., Testosterone undecanoate Andriol®), that are currently on the market. Moreover, the present oral formulations show a reduced inter-individual variability of the plasma concentrations observed after administration in humans. Finally, because of their high stability during storage, our formulations can be produced and provided to the user as ready-to-use solutions, easily administered and less expensive with respect to solid forms, due to the fact that no lyophilization is forseen.

DETAILED DESCRIPTION OF THE INVENTION

Figure 1:
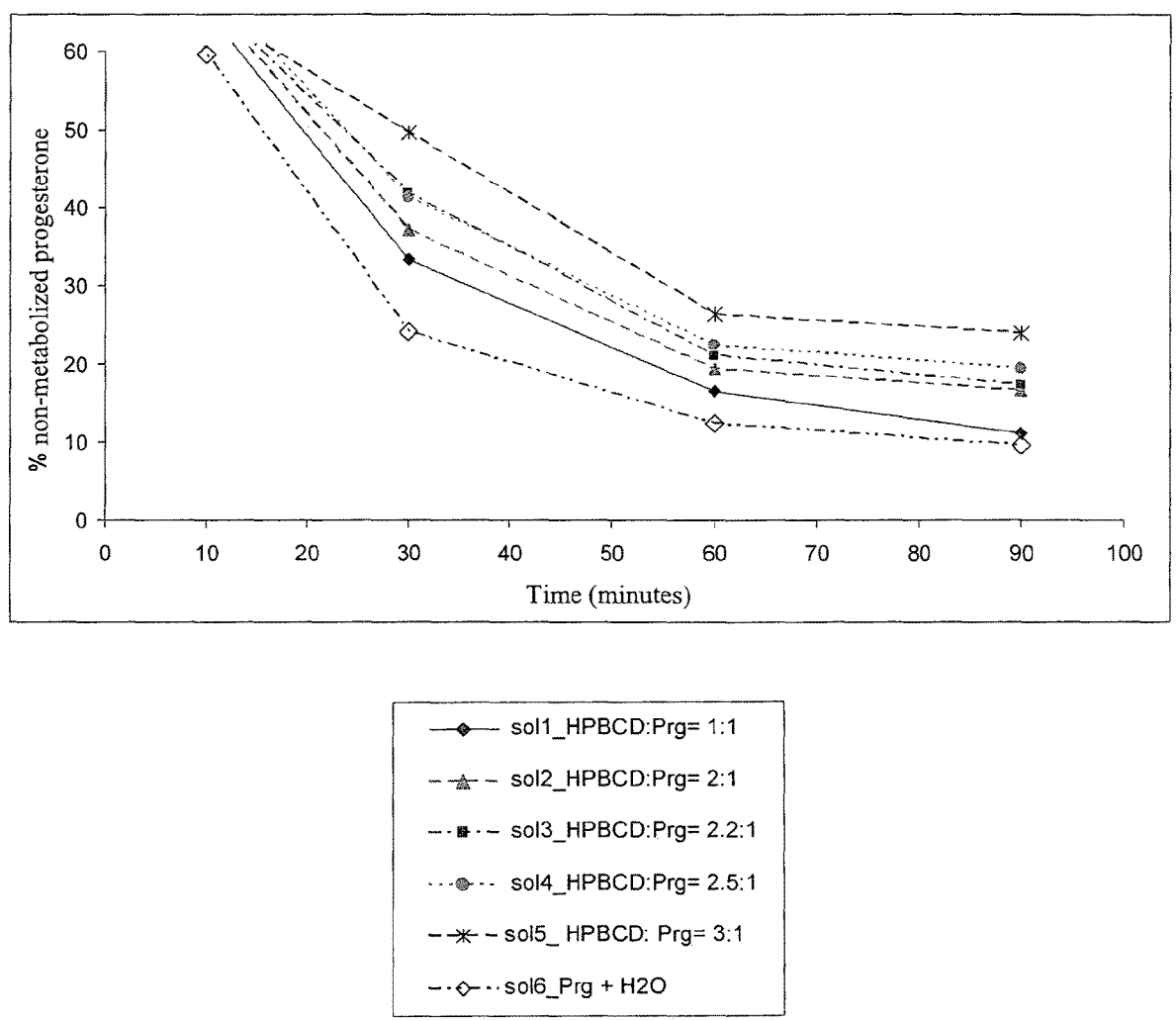
FIG. 1: Percentage of unmodified Progesterone (not metabolised) over time after incubation in human hepatic microsomes at 37° C. of solutions with different molar ratios between HPβCD and Prg.

The steroid hormones used in the present invention are Progesterone (Prg), Testosterone (Tst), and derivatives thereof.

The hydroxypropyl-β-cyclodextrin (HPβCD) used contains a residue of unsubstituted β-cyclodextrin that is lower than 0.3% by weight, with respect to the HPβCD. Methods for obtaining HPβCD with this low impurity level are described for example in US 2006/0058262. The complexes of the invention, obtained by means of the same, lead to stable solutions at room temperature for at least 24 months.

In the complexes of the invention, the molar ratio between HPβCD and Progesterone or Testosterone, can vary as follows:

a) (HPβCD:Progesterone): comprised between 1.7:1 and 2.4:1, preferably between 1.9:1 and 2.1:1, most preferably about 2:1; or b) (HPβCD:Testosterone): comprised between 1.7:1 and 3.0:1, preferably between 1.9:1 and 2.1:1, most preferably about 2:1.

(i) The invention therefore concerns pharmaceutical compositions for use in the oral administration of steroid hormones, comprising a complex of hydroxypropyl-β-cyclodextrin (HPβCD) as described in paragraphs (a) or (b) above, (ii) The invention further concerns oral pharmaceutical compositions comprising a complex of hydroxypropyl-β-cyclodextrin (HPβCD) as described in paragraphs (a) or (b) above, for use in the treatment of diseases requiring progesterone or testosterone treatment.

(iii) The invention further concerns the use of a complex of hydroxypropyl-β-cyclodextrin (HPβCD) as described in paragraphs (a) or (b) above, for the manufacture of an oral pharmaceutical composition for treating diseases requiring progesterone or testosterone treatment.

(iv) The invention further includes a method to improve the bioavailability of an orally administrable/administered progesterone or testosterone, characterized by formulating said progesterone or testosterone as a complex of hydroxypropyl-β-cyclodextrin (HPβCD) as described in paragraphs (a) or (b) above.

The invention further includes the compositions, uses and methods listed in paragraphs (i)-(iv) above, characterized in that the complex is not administered by routes other than the oral route.

The invention further includes the compositions, uses and methods listed in paragraphs (i)-(iv) above, further characterized in that said oral pharmaceutical composition is formulated in one or more dosage units, each containing less than 100 mg of hormone (progesterone or testosterone) per gram of solution, e.g. between 5 an 100 mg/g, preferably between 5 and 50 mg/g of, more preferably between 15 and 40 mg/g, calculated as non-complexed form.

The term "oral administration" used herein means, as usually understood in pharmacology, the administration of a composition which is simply and directly swallowed though the esophagus into the stomach, without permanence in the mouth cavity, whereby the absorption of the drug takes place naturally in the gastro-intestinal tract, as opposed to e.g. the boccal/sublingual route, in which the gastro-intestinal absorption is undesired, and absorption takes place via the mouth cavity.

Examples of diseases requiring progesterone treatment are, without limitation: endometrial hyperplasia, premenstrual syndrome, treatment of the symptoms of menopause, treatment of infertile women needing luteal phase support as part of an Assisted Reproductive Technology (ART) treatment program, secondary amenhorrea, progesterone deficiency symptoms, pre-term birth, benign mastopathy, repeated abortion.

Examples of diseases requiring testosterone treatment are, without limitation: testosterone replacement therapy in male hypogonadal disorders, for example: eunuchoidism; hypopituitarism; endocrine impotence; male climacteric symptoms like decreased libido and decreased mental and physical activity; certain types of infertility due to disorders of spermatogenesis, post-castration disorders. Testosterone therapy may also be indicated in osteoporosis due to androgenic deficiency.

As observed in the experimental part, the ratios between HPβCD and progesterone/testosterone are important in order to obtain a high absorption level of the hormone in the gastrointestinal duct and a limited degree of metabolic inactivation. The complexes of progesterone or testosterone, typically those with a HPβCD:hormone molar ratio 2:1, were found to be absorbed more easily with respect to those with ratio 1:1, used as a reference. This is particularly unexpected since, as known from Zoppetti et al., *J Incl Phenom. Macrocycl Chem*, 2007, 57:283-288) the complex 2:1 is much more stable with respect to the complex 1:1 (formation constant=111473 $m^{-1}$ and 3478 $m^{-1}$, respectively) and therefore considered less prone to make the hormone available for absorption. The data is further unexpected, due to the fact that it goes against other publications (see Dahan et al., *J Pharm Sci*, 99(6), 2010), according to which the increase of cyclodextrin leads to a corresponding reduction of the permeation of the drug through the membrane. On the other hand, it has been found here that the extent of permeation of the steroid hormone through membranes is not linear when the concentration of HPβCD varies, but, on the contrary, a bell-shape curve can be observed with a permeation peak at an intermediate HPβCD: hormone 2:1 molar ratio. The aforementioned molar ratios also identify complexes that are sufficiently resistant to the metabolic inactivation in vitro.

The formation of the aforementioned complexes occurs according to per se known modalities. In general, HPβCD can be dissolved at room temperature and under stirring in a suitable amount of water, for example in a weight ratio in water comprised between 1:2 and 2:2; then the steroid hormone is added to the solution thus obtained, again under stirring, in a molar ratio with the HPβCD comprised in the ranges defined above; optionally, it is possible to add further water so as to obtain the desired volume/concentration of the final solution. In a non-limiting manner, the final solution can have a concentration of hormones present that is comprised between 5 and 100 mg/g, preferably between 5 and 50 mg/g, more preferably between 15 and 40 mg/g of solution. Other concentrations can be selected as a function of the final use.

The compositions of the invention thus obtained are typically in the liquid form, or rather aqueous solutions, comprising the complexes described above dissolved or substantially dissolved in the aqueous phase. The compositions contain, in addition to the aforementioned characteristic components, further additives as a function of the type of formulation desired. Among these additives, it is worth mentioning aromas, sweeteners, co-solvents, stabilisers, preservatives, emulsifiers, etc., underlining that such additives are merely optional, or rather, they are not essential for ensuring the stability and bioavailability of the complexes in solution, which is typical of the complexes as such.

Because of their high stability, the HPβCD/hormone solutions can be provided to the user already in the liquid and ready-to-use form; it is however also possible to prepare and store the formulation in a suitable concentrated solid or liquid form, to be added with a suitable volume of water at the moment of use. For example, a kit can be foreseen comprising a pre-formulation, for example in the form of powder, granules, or a concentrated solution, that is associated with a container containing the necessary volume of aqueous solution for an extemporaneous reconstitution of the formulation. The solution object of the invention can be dispensed in normal single-dose or multidose containers made from glass or plastic material and can be safely stored at room temperature for at least 24 months.

EXPERIMENTAL PART

Example 1A—Preparation of Aqueous Solutions of Progesterone and HPβCD with Different Molar Ratios at the Nominal Concentration of Progesterone of 32 mg/g Solution 1: Solution with Molar Ratio HPβCD:Progesterone 1:1

2.3684 g of HPβCD (content of β unsubstituted cyclodextrin present in the HPβCD lower than 0.3%) were dissolved in 4.0070 g of water under magnetic stirring and, again under stirring, 0.5018 g of Progesterone were added. When the dissolution was obtained, 8.5028 g of water were added. The final concentration of Progesterone was 0.0326 g/g.

Solution 2: Solution with Molar Ratio HPβCD:Progesterone 2:1

4.7371 g of HPβCD (content of unsubstituted β cyclodextrin present in the HPβCD lower than 0.3%) were dissolved in 6.0048 g of water under magnetic stirring and, again under stirring, 0.5019 g of Progesterone were added. When the dissolution was obtained 4.0082 g of water were added. The final concentration of Progesterone was of 0.0329 g/g.

Solution 3: Solution with Molar Ratio HPβCD:Progesterone 2.2:1

5.2053 g of HPβCD (content of unsubstituted β cyclodextrin present in the HPβCD lower than 0.3%) were dissolved in 6.5008 g of water under magnetic stirring and, again under stirring, 0.5017 g of Progesterone were added. When the dissolution was obtained 3.0014 g of water were added. The final concentration of Progesterone was 0.0330 g/g.

Solution 4: Solution with Molar Ratio HPβCD:Progesterone 2.5:1

5.9154 g of HPβCD (content of unsubstituted β cyclodextrin present in the HPβCD lower than 0.3%) were dissolved in 8.0026 g of water under magnetic stirring and, again under stirring, 0.5018 g of Progesterone were added. When the dissolution was obtained 1.0081 g of water were added. The final concentration of Progesterone was 0.0325 g/g.

Solution 5: Solution with Molar Ratio HPβCD:Progesterone 3:1

7.1015 g of HPβCD (content of unsubstituted β cyclodextrin present in the HPβCD lower than 0.3%) were dissolved in 8.0082 g of water under magnetic stirring and, subsequently under stirring 0.5020 g of Progesterone were added.

The concentration of Progesterone was 0.0322 g/g.

Solution 6: Solution of Progesterone in Water

Under magnetic stirring 0.5018 g of Progesterone were dispersed in 15.0016 g of water.

The final concentration of Progesterone was 0.0324 g/g.

Example 1B—Microsomal Degradation Tests

The solutions of progesterone (1, 2, 3, 4, 5, 6) shown above in example 1A were diluted with water until a working concentration of 397.5 μM was obtained.

The microsomes used in the study have an initial protein concentration of 20 mg/mL in a Sucrose solution with a concentration of 250 mM.

The sample solution was prepared by adding, in a plastic test tube, in the following order: 2 μL of magnesium chloride 165 mM ($MgCl_2$), 10 μL of the solution object of the study (1, 2, 3, 4, 5, 6) with a theoretical concentration of Progesterone of 397.5 μM, 73 μL of phosphate buffer pH 7.4 and 10 μL of solution NADPH 13 mM. The final concentration of the progesterone was of 39.75 μM, whereas that of the cofactor NADPH was of 1.3 mM.

The reaction started at the moment in which 5 μL of preincubated microsomes (20 mg/mL) were added, at the temperature of 37° C. for 3 minutes, to the sample solution in the test tube. The final concentration of protein was of 1 mg/mL.

The reaction was kept at a controlled temperature of 37° C. and under bland stirring.

The metabolic degradation reaction was stopped after 0, 10, 30, 60, 90 minutes adding 300 μL of Acetonitrile to 100 μL of the sample solution. The solutions thus obtained were centrifuged at 14000 rpm for 3 minutes and the supernatant underwent chromatographic analysis.

The HPLC-UV chromatographic analysis was carried out in isocratic flow at room temperature using a RP 18 column 5 μm 3.9×150 mm with mobile phase of Acetonitrile and Water in ratio 55 and 45. The operating wavelength was 241 nm, the flow 1 mL/min and the injection volume 20 μL.

Figure 4:
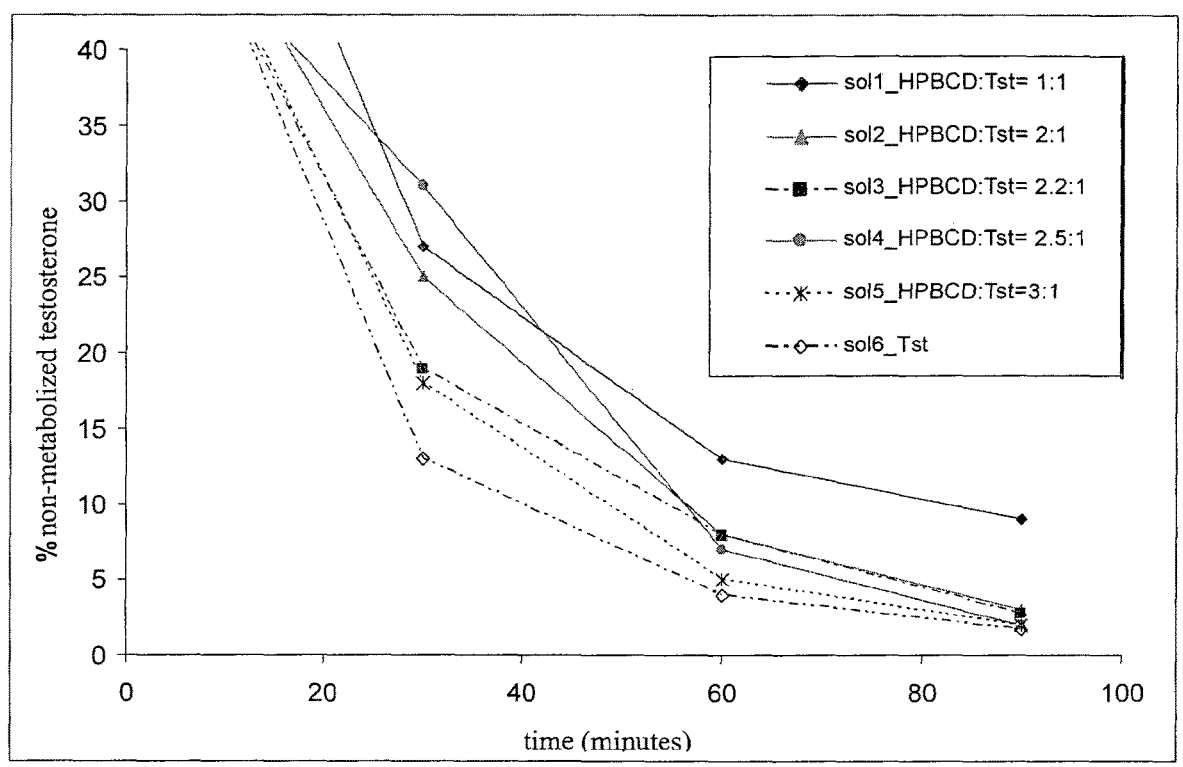
FIG. 4: Percentage of unmodified Testosterone (not metabolised) over time after incubation in human hepatic microsomes at 37° C. of solutions with different molar ratios between HPβCD and Tst

FIG. 1 shows the percentage of unmodified Progesterone (not degraded) over time after incubation at 37° C. with microsomes of human origin with the variation of the molar ratios between HPβCD and Progesterone. The detailed description of the experiment is shown in the example 1. From such results it can be seen that when the concentration of HpβCD is increased, with consequent variation of the molar ratio between Progesterone and HPβCD, the active substance is less degraded. It can be observed that the increase in concentration of HPβCD protects the Progesterone from metabolic activities. In an analogous manner the experiment was carried out on the solutions 1-6 of the example 4 relative to Testosterone leading to the result shown in FIG. 4.

Example 2—Preparation of Aqueous Solutions of Progesterone and HPβCD with Different Molar Ratios at the Nominal Progesterone Concentration of 20 mg/g Solution 1: Solution with Molar Ratio HPβCD:Progesterone 1:1

1.4252 g of HPβCD (content of unsubstituted β cyclodextrin present in the HPβCD lower than 0.3%) were dissolved in 3.0053 g of water under magnetic stirring and, again under stirring, 0.3028 g of Progesterone were added. When the dissolution was obtained, 10.2039 g of water were added. The final concentration of Progesterone was of 0.0203 g/g.

Solution 2: Solution with Molar Ratio HPβCD:Progesterone 2:1

2.8445 g of HPβCD (content of unsubstituted β cyclodextrin present in the HPβCD lower than 0.3%) were dissolved in 4.2073 g of water under magnetic stirring and, again under stirring, 0.3026 g of Progesterone were added. When the dissolution was obtained 7.6073 g of water were added. The final concentration of progesterone was of 0.0202 g/g.

Solution 3: Solution with Molar Ratio HPβCD:Progesterone 2.2:1

3.1255 g of HPβCD (content of unsubstituted β cyclodextrin present in the HPβCD lower than 0.3%) were dissolved in 5.0073 g of water under magnetic stirring and, again under stirring, 0.3049 g of Progesterone were added. When the dissolution was obtained 6.5028 g of water were added. The final concentration of Progesterone was of 0.0204 g/g.

Solution 4: Solution with Molar Ratio HPβCD:Progesterone 2.5:1

3.5548 g of HPβCD (content of unsubstituted β cyclodextrin present in the HPβCD lower than 0.3%) were dissolved in 6.0029 g of water under magnetic stirring and, again under stirring, 0.3031 g of Progesterone were added. When the dissolution was obtained 5.1053 g of water were added. The final concentration of Progesterone was of 0.0203 g/g.

Solution 5: Solution with Molar Ratio HPβCD:Progesterone 3:1

4.2670 g of HPβCD (content of unsubstituted β cyclodextrin present in the HPβCD lower than 0.3%) were dissolved in 7.0053 g of water under magnetic stirring and, subsequently, under stirring 0.3064 g of Progesterone were added. When the dissolution was obtained 3.4019 g of water were added.

The concentration of Progesterone was of 0.0205 g/g.

Solution 6: Solution of Progesterone in Water

Under magnetic stirring 0.3013 g of progesterone in 14.6575 g of water were dispersed.

The final concentration of Progesterone was of 0.0201 g/g.

Example 3—Preparation of Aqueous Solutions of Testosterone and HPβCD with Different Molar Ratios at the Nominal Concentration of Testosterone of 20 mg/g Solution 1: Solution with Molar Ratio HPβCD:Testosterone 1:1

1.5600 g of HPβCD (content of unsubstituted β cyclodextrin present in the HPβCD lower than 0.3%) were dissolved in 6.0062 g of water under magnetic stirring and, subsequently under stirring 0.3021 g of Testosterone were added. When the dissolution was obtained 6.6003 g of water were added.

The concentration of Testosterone was of 0.0209 g/g.

Solution 2: Solution with Molar Ratio HPβCD:Testosterone 2:1

3.1395 g of HPβCD (content of unsubstituted β cyclodextrin present in the HPβCD lower than 0.3%) were dissolved in 6.0060 g of water under magnetic stirring and, subsequently 0.3041 g of Testosterone were added under stirring. When the dissolution was obtained 5.0020 g of water were added.

The concentration of Testosterone was of 0.0210 g/g.

Solution 3: Solution with Molar Ratio HPβCD:Testosterone 2.2:1

3.4206 g of HPβCD (content of unsubstituted β cyclodextrin present in the HPβCD lower than 0.3%) were dissolved in 6.0077 g of water under magnetic stirring and, subsequently 0.3012 g of Testosterone were added under stirring. When the dissolution was obtained 4.8045 g of water were added.

The concentration of Testosterone was of 0.0207 g/g.

Solution 4: Solution with Molar Ratio HPβCD:Testosterone 2.5:1

3.8857 g of HPβCD (content of unsubstituted β cyclodextrin present in the HPβCD lower than 0.3%) were dissolved in 6.0007 g of water under magnetic stirring and, subsequently 0.3011 g of Testosterone were added under stirring. When the dissolution was obtained, 4.2050 g of water were added.

The concentration of Testosterone was of 0.0209 g/g.

Solution 5: Solution with Molar Ratio HPβCD:Testosterone 3:1

4.6613 g of HPβCD (content of unsubstituted β cyclodextrin present in the HPβCD lower than 0.3%) were dissolved in 6.0070 g of water under magnetic stirring and, subsequently 0.3010 g of Testosterone were added under stirring. When the dissolution was obtained 3.2041 g of water were added.

The concentration of Testosterone was of 0.0212 g/g.

Solution 6: Solution of Testosterone in Water

Under magnetic stirring 0.3025 g of Testosterone were dispersed in 14.4962 g of water.

The final concentration of Testosterone was of 0.0204 g/g.

Example 4—Preparation of Aqueous Solutions of Testosterone and HPBCD with Different Molar Ratios at the Nominal Concentration of Testosterone of 35 mg/g Solution 1: Solution with Molar Ratio HPβCD:P Testosterone 1:1

3.2091 g of HPβCD (content of unsubstituted β cyclodextrin present in the HPβCD lower than 0.3%) were dissolved in 7.0070 g of water under magnetic stirring and, subsequently under stirring 0.6218 g of Testosterone were added. When the dissolution was obtained 6.9264 g of water were added.

The concentration of Testosterone was of 0.0350 g/g.

Solution 2: Solution with Molar Ratio HPβCD:Testosterone 2:1

6.4156 g of HPβCD (content of unsubstituted β cyclodextrin present in the HPβCD lower than 0.3%) were dissolved in 7.0059 g of water under magnetic stirring and, subsequently under stirring 0.6218 g of Testosterone were added. When the dissolution was obtained 3.7234 g of water were added.

The concentration of Testosterone was of 0.0350 g/g.

Solution 3: Solution with Molar Ratio HPβCD:Testosterone 2.2:1

7.0702 g of HPβCD (content of unsubstituted β cyclodextrin present in the HPβCD lower than 0.3%) were dissolved in 7.0010 g of water under magnetic stirring and, subsequently under stirring 0.6226 g of Testosterone were added. When the dissolution was obtained 3.0966 g of water were added.

The concentration of Testosterone was of 0.0350 g/g.

Solution 4: Solution with Molar Ratio HPβCD:Testosterone 2.5:1

8.0255 g of HPβCD (content of unsubstituted β cyclodextrin present in the HPβCD lower than 0.3%) were dissolved in 9.0089 g of water under magnetic stirring and, subsequently under stirring 0.6219 g of Testosterone were added. When the dissolution was obtained 0.1241 g of water were added.

The concentration of Testosterone was of 0.0350 g/g.

Solution 5: Solution with Molar Ratio HPβCD:Testosterone 3:1

9.6645 g of HPβCD (content of unsubstituted β cyclodextrin present in the HPβCD lower than 0.3%) were dissolved in 10.4679 g of water under magnetic stirring and, subsequently under stirring 0.6325 g of Testosterone were added. The concentration of Testosterone was of 0.0305 g/g.

Solution 6: Solution of Testosterone in Water

Under magnetic stirring 0.6213 g of Testosterone were dispersed in 17.1358 g of water.

The final concentration of Testosterone was of 0.0350 g/g.

Example 5—Permeation Study of the Solutions with Different Molar Ratios Between HPβCD and Progesterone and Between HPβCD and Testosterone The solutions (1, 2, 3, 4, 5, 6), the preparation of which is shown in Examples 1A, 2, 3 and 4 underwent permeation analysis through suitable membranes such as to emulate the gastrointestinal mucous.

The study was carried out using the Franz Cell diffusion system.

The receptor has a volume of 7 mL and made up of a solution of 77% Ethanol and 23% water. The available permeation area of each of the 6 cells of the system was of 1.767 $cm^2$. The stirring velocity of the system was of 400 rpm and the temperature was kept constant at 37° C.

The preparation of the Franz Cell system was completed by arranging the membrane between the receptor and the donor. In the donor of each cell 1 mL of the studied solutions, drawn under stirring, was introduced.

During the permeation analysis, not only the solution of the receptor, but also the solutions 1÷6 present above the membrane were kept under stirring.

At withdrawal times of 1, 2, 3, 4, 5, 6, 8, 10, 12, 16, 20, 24 hours, permeate aliquots were collected from every cell (total volume withdrawn by the system from the receptor solution 2.5 mL, the sampling volume of which is 1.0 mL) and directly analysed with liquid chromatography at high pressure (HPLC) with a UV detector. In the Franz Cell system used, after sampling, the receptor solution was restored by the amount withdrawn.

For each aliquot collected, the amount of permeated hormone was analysed with the validated HPLC-UV method.

The amount of permeated progesterone was calculated starting from a calibration curve in the concentration range of 0.0378÷503.896 µg/mL whereas for Testosterone the calibration curve was in the concentration range of 0.0223÷514.925 µg/mL.

FIGS. 2, 3, 4 and 5 show the performance of the permeated hormone by unit area as a function of the drawing times considering the amount of hormone present by unit weight of solution.

Figure 2:
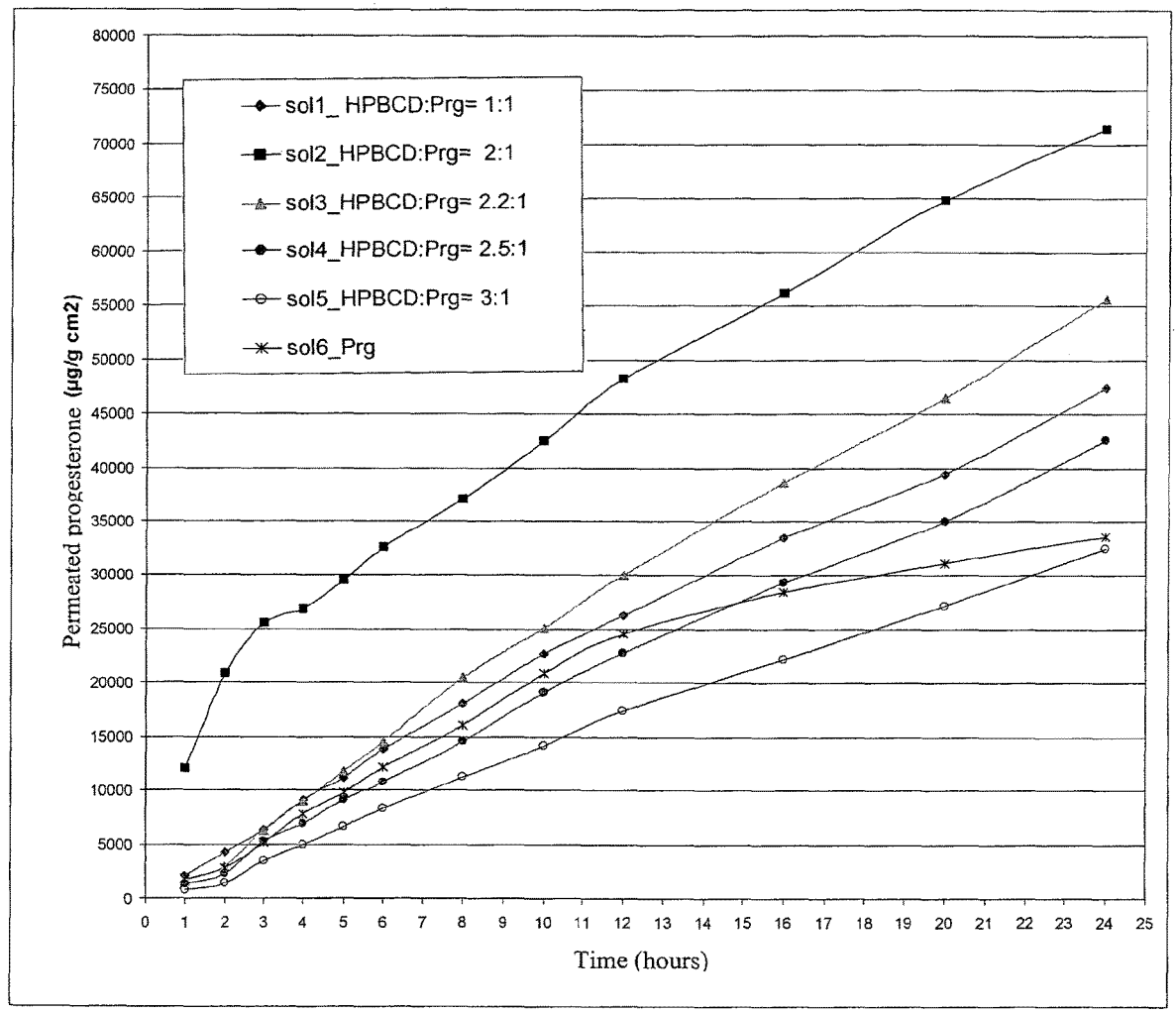
FIG. 2: Permeation profile of Progesterone through artificial silicone membranes. Different solutions have been tested characterised by different molar ratios between HPβCD and Prg at the concentration of Progesterone of 32 mg/g
Figure 3:
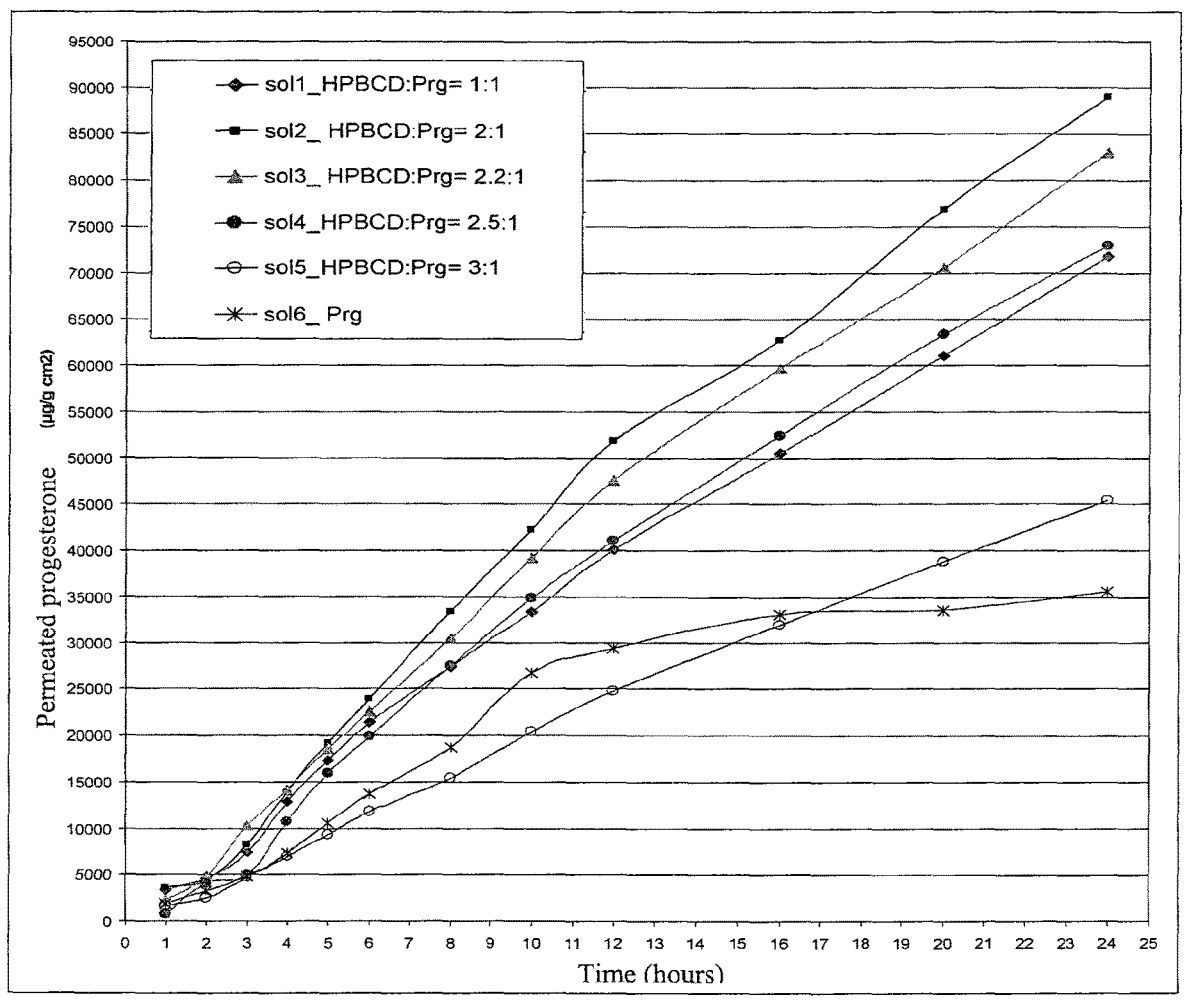
FIG. 3: Permeation profile of Progesterone through artificial silicone membranes. Different solutions have been tested characterised by different molar ratios between HPβCD and Prg at the concentration of Progesterone of 20 mg/g.
Figure 9:
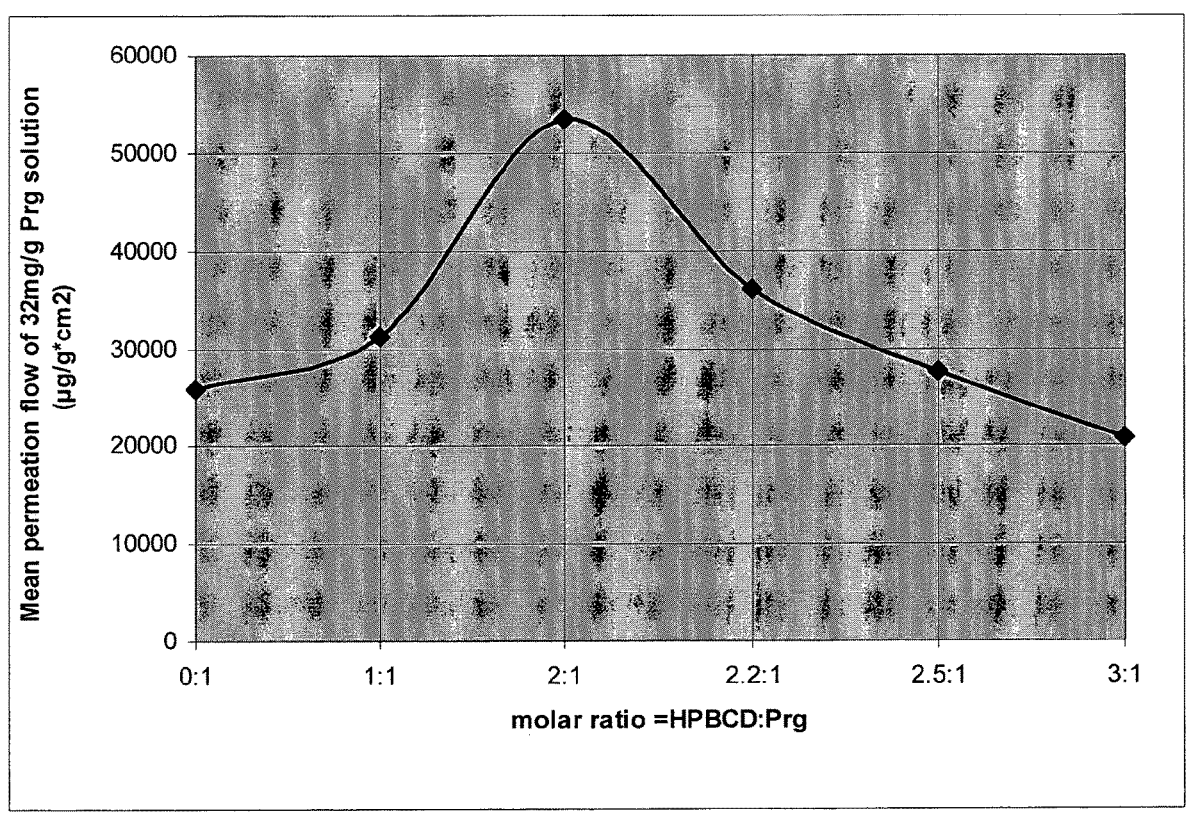
FIG. 9: reproduction of the data of FIG. 2, shown mean permeation flow rate of Progesterone 32 mg/g formulated as aqueous solutions of HPβCD:Progesterone as a function of the growing molar ratio.

The results, shown in FIG. 2, (also reproduced in FIG. 9 as a function of the growing ratios between HPβCD and Pgr) highlight the obtaining of the best permeation values within an intermediate range of molar ratios between HPβCD and Pgr, with the best values between 2:1 and 2.2:1. Therefore the permeability does not vary in a manner that is proportional to the amount of HPβCD, but is maximised at the values of the intermediate ratio levels between HPβCD and hormone, highlighted here.

The best permeation values found here correspond to molar ratios between HPβCD and steroid hormone at which the degradative metabolism is already considerably inhibited by the presence of cyclodextrin (see the data of the example 1B); therefore, the optimal permeation effect, found here at molar ratios between HPβCD and hormone around 2:1, is added to that of a limited degradative metabolism at the gastrointestinal mucous level.

Figure 10:
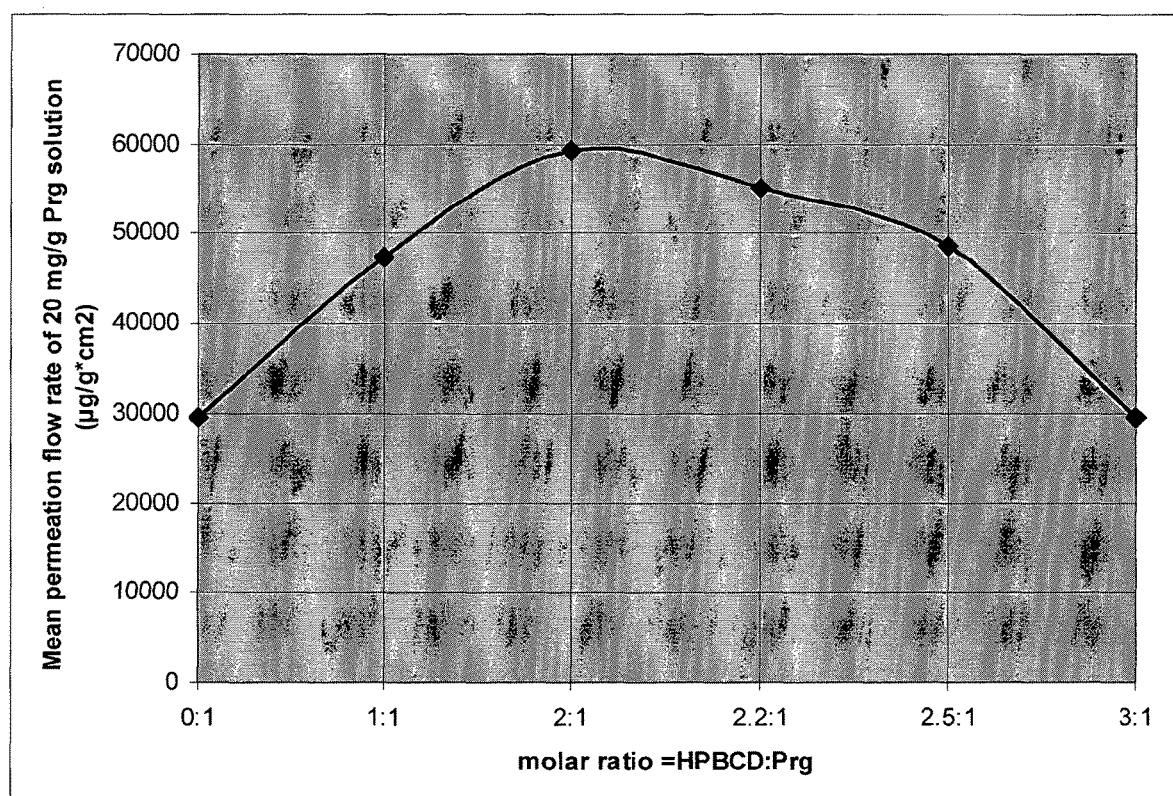
FIG. 10: reproduction of the data of FIG. 3, shown mean permeation flow rate of Progesterone 20 mg/g formulated as aqueous solutions of HPβCD:Progesterone as a function of the growing molar ratio.

In FIG. 2 the concentration of Progesterone used in the 6 solutions with different molar ratios between HPβCD and Prg is of 32 mg of Progesterone per gram of solution. Moreover FIG. 9 highlights that the comparative 1:1 complexes (theoretically more prone to hormone permeation) permeated worse than the complexes in accordance with the invention. An analogous result, shown in FIG. 3 (cf. also FIG. 10) was obtained by repeating such an experiment with a different concentration of Progesterone, 20 mg/g. These results confirm that the permeability of Progesterone is influenced by the molar ratio between HPβCD and Prg and not by the concentration of the complex in solution.

Figure 5:
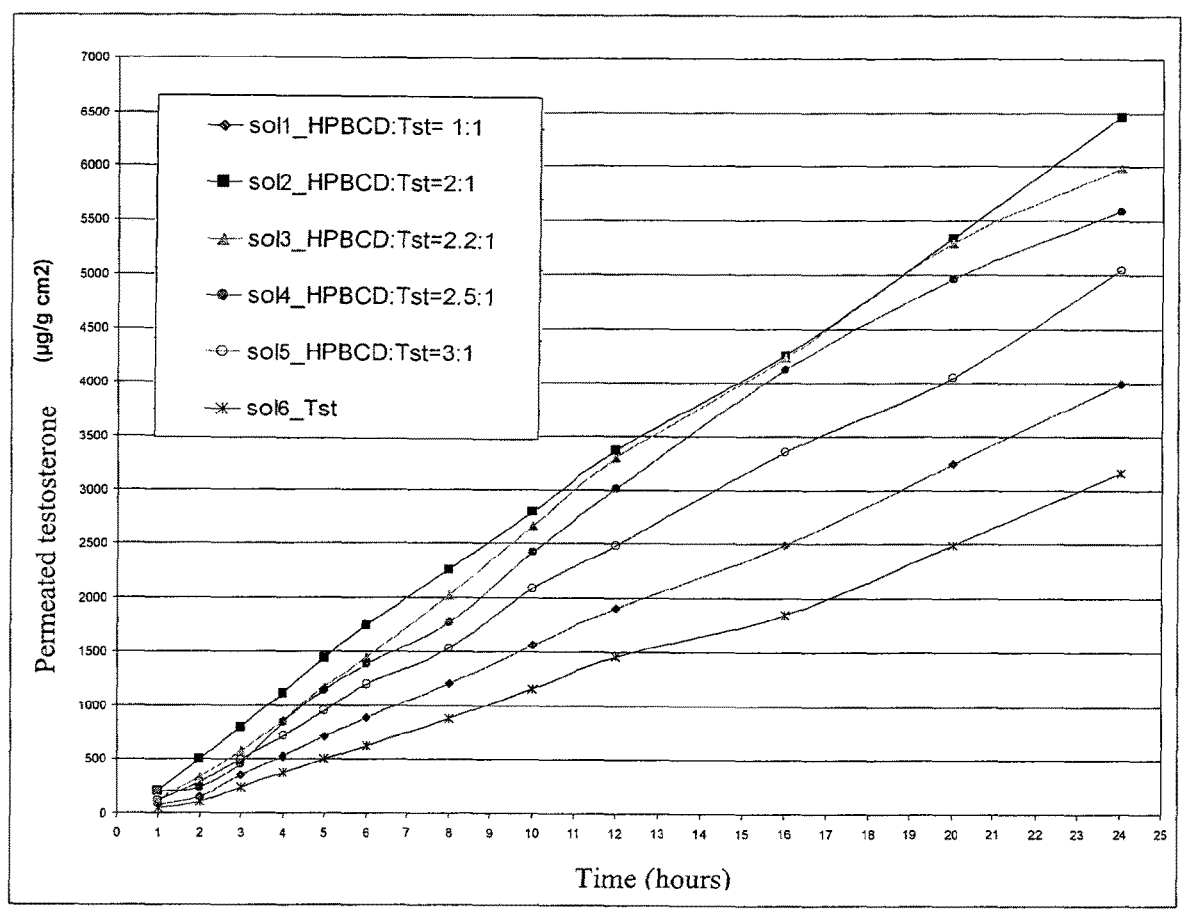
FIG. 5: Permeation profile of Testosterone through artificial silicone membranes. Different solutions have been tested characterised by different molar ratios between HPβCD and Tst at the concentration of Testosterone of 20 mg/g.
Figure 6:
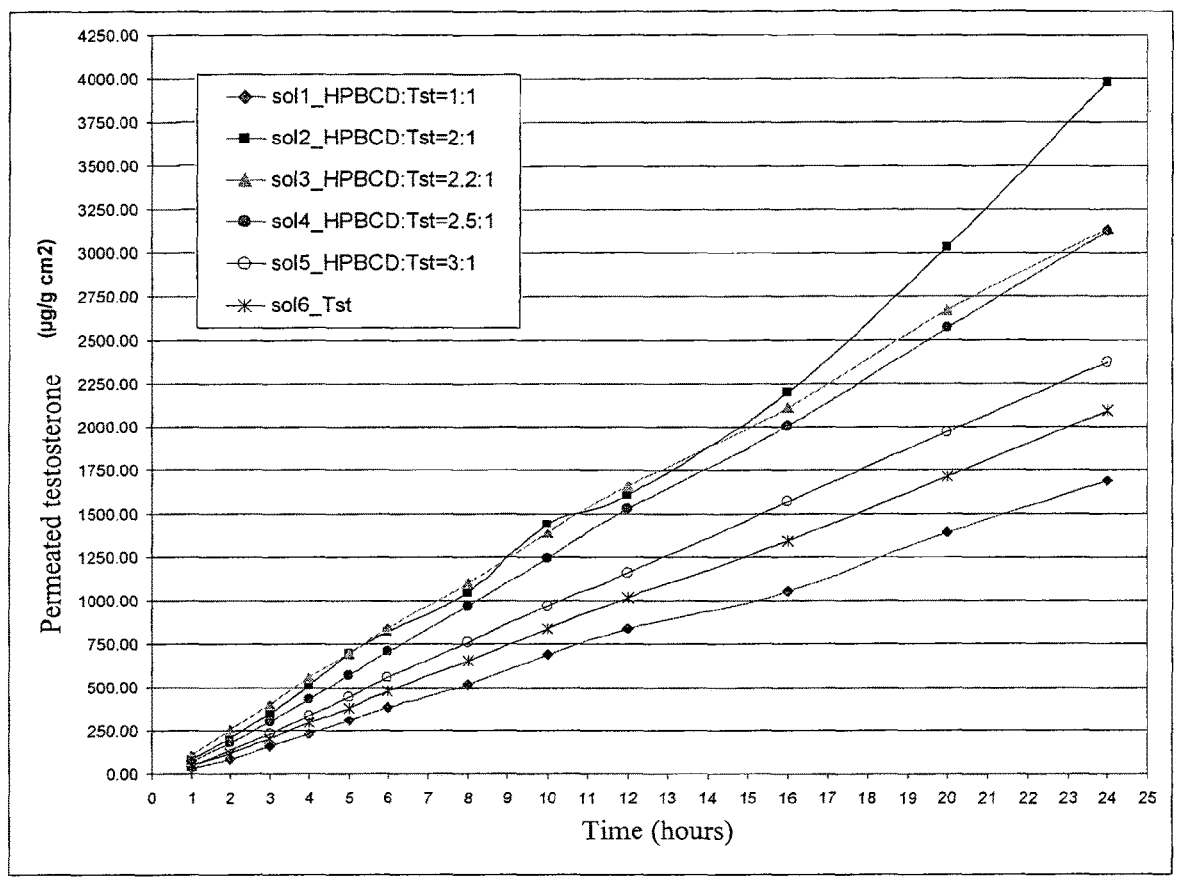
FIG. 6: Permeation profile of Testosterone through artificial silicone membranes. Different solutions have been tested characterised by different molar ratios between HPβCD and Tst at the concentration of Testosterone of 35 mg/g

Similar results were found in the case of Testosterone: in particular, FIGS. 5 and 6 highlight the obtaining of optimal permeability values for molar ratios HβCD:Testosterone of around 2:1.

Example 6 Stability Tests

A solution with molar ratio HPβCD:Prg=2:1 was obtained by dissolving, in a suitable dissolver, 2720 g of HPβCD (content of unsubstituted β cyclodextrin present in HPβCD lower than 0.3%) in 5000 g of water and then adding 272 g of Progesterone. When the dissolution was obtained 5000 g of water were added. The final concentration of Progesterone determined through HPLC/UV analysis was of 20.61 mg/g. The solution thus obtained undergoes filtration in series through filters of 0.45 and 0.22 µm and is subsequently separated in vials filled with a volume such as to ensure a dose of Progesterone for vials of 25 mg. The solution has a density of 1.0675 g/mL. The vials were closed hermetically and underwent a stability study in ICH conditions at the temperature of 25° C./60% R.H.

As illustrated in table 1, the solution was stable for at least 24 months without undergoing considerable variations in the amount of Progesterone.

TABLE 1

Stability data of the aqueous solution of Progesterone and HPβCD with a molar complexation ratio HPβCD:Prg 2:1

| | | 25° C. ± 2° C./60% ± 5% R.H | | | | | | |
|---|---|---|---|---|---|---|---|---|
| Analysis | Specification | 0 | 3 m | 6 m | 9 m | 12 m | 18 m | 24 m |
| Progesterone Identification (HPLC) | Positive | Positive | Positive | Positive | Positive | Positive | Positive | Positive |
| Progesterone Assay | 95.0-105.0% of the theoretical value at release 90.0-105.0% of the theoretical value during stability study | 100.3% | 99.5% | 102.1% | 101.3% | 100.5% | 101.0% | 99.5% |
| Each individual unknown impurity | ≤0.5% | <0.1% | <0.1% | <0.1% | 0.1% | 0.1% | 0.1% | 0.1% |
| Total Impurities | ≤0.8% | <0.1% | 0.1% | 0.1% | 0.1% | 0.1% | 0.1% | 0.2% |
| Endotox (LAL Test) | <1.0 EU/mg | <0.2 EU/mg | NA | <0.2 EU/mg | NA | <0.2 EU/mg | NA | <0.2 EU/mg |

Example 7 Comparative Pharmacokinetic Tests

Figure 7:
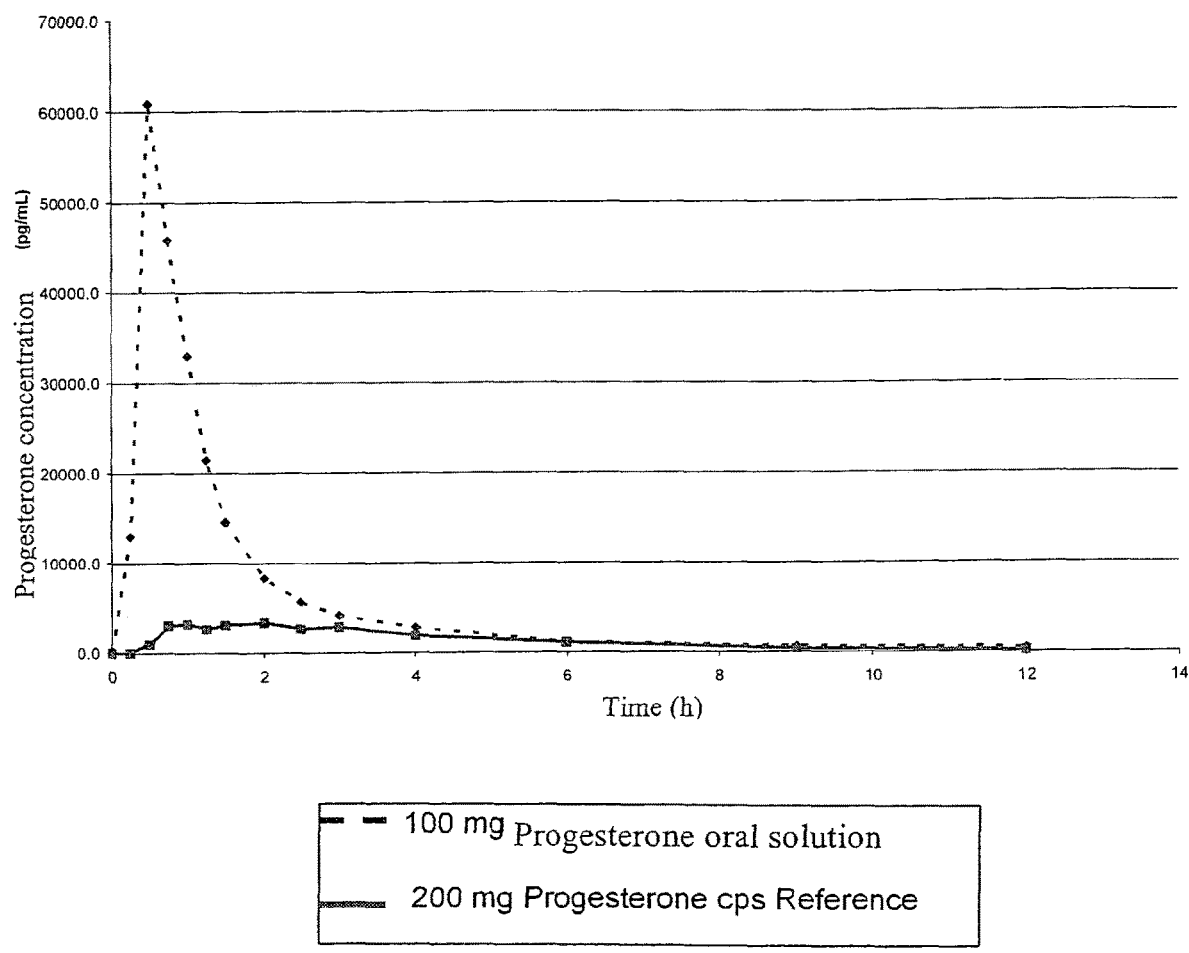
FIG. 7: Comparative plasma pharmacokinetic profiles of Progesterone in a healthy patient after oral administration of the solution of hydroxypropyl-β-cyclodextrin with Prg in molar ratio 2:1 and of the oral formulation present on the market (Prometrium).

The solution described in example 6 was used in a comparative clinical pharmacokinetic study (FIG. 7, Tables 2 and 3). Four female volunteers in post-menopausal age, non- or ex-smokers, with an age of between 18 and 75 years received, according to a crossover design, a single dose of 100 mg of Progesterone dissolved in the aforementioned solution or of 200 mg of Progesterone in soft capsules (reference formulation on the market, Prometrium). Tables 2 and 3 show the results of the pharmacokinetic parameters obtained from the clinical study: Table 2 refers to the formulation object of the present patent whereas Table 3 refers to the commercial reference formulation (Prometrium).

The results in Table 2 prove that the present composition generates an overall exposure per unit dose (AUC/dose) approximately 9 times higher than that obtained with the Reference formulation (Table 3) and an average peak concentration ($C_{max}$) about 30-fold higher; moreover, the peak time ($t_{max}$) achieved with the progesterone solution is substantially lower.

Moreover, plasma levels of Progesterone observed for the formulation object of the present invention (average $C_{max}$ 60 ng/mL ca. for a dose of 100 mg Progesterone) are in line with those which were reported in the already mentioned patent of Pitha et al., in which a dose of 100 mg Progesterone administered in form of a HPβCD:Prg 1:1 complex via buccal route—therefore without hepatic first-pass effect— gave a $C_{max}$ of around 50 ng/mL. This confirms that the complexes of the invention maintain a remarkable bioavailability, despite being likely subject to gastro-intestinal and hepatic first-pass metabolism. A dose-effective treatment of progesterone/testosterone complexes with HPβCD via the oral route (more patient-friendly than e.g. the sublingual/buccal/nasal route) is therefore obtained. As a further advantage, the composition of the invention makes it possible to significantly reduce the inter-individual variability of the plasma levels, expressed in the table by the CV % value of AUC and $C_{max}$, with respect to the commercial formulation of Table 3.

TABLE 2

PK parameters of Progesterone administered as an oral solution complexed with HPβCD, ratio 2:1

| Subject | $C_{max}$ (pg/mL) | $t_{max}$ (h) | AUC (pg · h/mL) | $t_{1/2,z}$ (h) | $C_{max}$/Dose | AUC/Dose |
|---|---|---|---|---|---|---|
| 1 | 57325.1 | 0.5 | 77021.2 | 5.21 | 11465.02 | 15404.24 |
| 2 | 63841.2 | 0.5 | 91656.5 | 4.79 | 12768.24 | 18331.30 |
| 3 | 63192.8 | 0.5 | 62893.8 | 3.85 | 12638.56 | 12578.76 |
| 4 | 59081.4 | 0.5 | 56407.4 | 5.11 | 11816.28 | 11281.48 |
| Mean | 60860.1 | 0.5 | 71994.7 | 4.7 | 12172.0 | 14398.9 |
| min | 57325.1 | 0.5 | 56407.4 | 3.9 | 11465.0 | 11281.5 |
| max | 63841.2 | 0.5 | 91656.5 | 5.2 | 12768.2 | 18331.3 |
| SD | 3161.7 | 0.0 | 15680.6 | 0.6 | 632.3 | 3136.1 |
| CV % | 5.2 | 0.0 | 21.8 | 13.1 | 5.2 | 21.8 |

TABLE 3

PK parameters of Progesterone, reference formulation (Prometrium)

| Subject | $C_{max}$ (pg/mL) | $t_{max}$ (h) | AUC (pg · h/mL) | $t_{1/2,z}$ (h) | $C_{max}$/Dose | AUC/Dose |
|---|---|---|---|---|---|---|
| 1 | 1912.6 | 0.75 | 6686.4 | 1.22 | 191.26 | 668.64 |
| 2 | 3925.4 | 1 | 13518.3 | 2.53 | 392.54 | 1351.83 |
| 3 | 8065.4 | 2 | 34464.2 | 1.83 | 806.54 | 3446.42 |
| 4 | 2323.5 | 1 | 9737.2 | 2.42 | 232.35 | 973.72 |
| Mean | 4056.7 | 1.2 | 16101.5 | 2.0 | 405.7 | 1610.2 |
| min | 1912.6 | 0.8 | 6686.4 | 1.2 | 191.3 | 668.6 |
| max | 8065.4 | 2.0 | 34464.2 | 2.5 | 806.5 | 3446.4 |
| SD | 2810.0 | 0.6 | 12556.7 | 0.6 | 281.0 | 1255.7 |
| CV % | 69.3 | 46.7 | 78.0 | 30.2 | 69.3 | 78.0 |

Therefore the formulation object of the present patent, characterised by an excellent bioavailability of the hormones contained in it, makes it possible to achieve high and effective plasma concentrations after oral administration of doses that are lower with respect to oral formulations currently on the market (e.g. Prometrium, Andriol), and with a greater reproducibility of the relative plasma curves, thus leading to a clear advantage in terms of compliance of the patient and of effectiveness and safety of the treatment.

Example 8—Preparation of Aqueous Solutions of Testosterone and HPβCD with Different Molar Ratios at the Nominal Concentration of Testosterone of 26 mg/g Solution 1: Solution with Molar Ratio HPβCD:Testosterone 2:1

In a suitable dissolver, 4.13 g of HPβCD (content of unsubstituted β cyclodextrin present in HPβCD lower than 0.3%) were dissolved in 4.48 g of water, subsequently 0.4 g of Testosterone were added. When the dissolution was obtained 6.38 g of water was added. The solution obtained was filtered through filter of 0.45 μm and subsequently separated in vials filled with a volume such as to ensure a dose of Testosterone for vials of 26 mg. The final concentration of Testosterone in the vial determined trough HPLC/UV analysis was of 26.0 mg/g.

The vials were closed hermetically and underwent a stability study in ICH conditions at the temperature of 25° C./60% R.H.

As illustrated in table 4, the solution was stable for at least 24 months without undergoing considerable variations in the amount of Testosterone.

TABLE 4

Stability data of the aqueous solution of Testosterone and HPβCD with a molar complexation ratio HPβCD:Tst 2:1

| | | 25° C. ± 2° C./60% R.H. | | | | | | |
|---|---|---|---|---|---|---|---|---|
| Analysis | Specification | 0 | 3 m | 6 m | 9 m | 12 m | 18 m | 24 m |
| Testosterone Identification (HPLC) | Positive | Positive | Positive | Positive | Positive | Positive | Positive | Positive |
| Testosterone Assay | 95.0-105.0% of the theoretical value at release 90-105% of the theoretical value during stability study | 101.00 | 101.10 | 100.67 | 100.27 | 100.31 | 100.14 | 99.95 |
| Each individual unknown impurity | ≤0.2% | <0.1% | <0.1% | <0.1% | 0.1% | 0.1% | 0.1% | 0.1% |
| Total Impurities | ≤2.0% | 0.5% | 0.5% | 0.5% | 0.7% | 0.7% | 0.7% | 0.8% |
| TAMC | ≤100 CFU/g | <1 CFU/g | <1 CFU/g | <1 CFU/g | <1 CFU/g | <1 CFU/g | <1 CFU/g | <1 CFU/g |
| TYMC | ≤100 CFU/g | <1 CFU/g | <1 CFU/g | <1 CFU/g | <1 CFU/g | <1 CFU/g | <1 CFU/g | <1 CFU/g |
| *Escherichia Coli* | Absent/g | Absent/g | Absent/g | Absent/g | Absent/g | Absent/g | Absent/g | Absent/g |

Solution 2: Solution with Molar Ratio HPβCD:Testosterone 3:1

In a suitable dissolver, 6.195 g of HPβCD (content of unsubstituted cyclodextrin present in HPβCD lower than 0.3%) were dissolved in 6.75 g of water, subsequently 0.4 g of Testosterone were added. When the dissolution was obtained 2.041 g of water was added. The solution obtained was filtered through filter of 0.45 μm and subsequently separated in vials filled with a volume such as to ensure a dose of Testosterone for vials of 26 mg. The final concentration of Testosterone in the vial determined trough HPLC/UV analysis was of 26.0 mg/g.

The vials were closed hermetically and underwent a stability study in ICH conditions at the temperature of 25° C./60% R.H.

As illustrated in table 5, the solution was stable for at least 24 months without undergoing considerable variations in the amount of Testosterone.

TABLE 6-continued

PK parameters of Testosterone administered as an oral solution completed with HPβCD, ratio 2:1

| Subject | $C_{max}$ (pg/mL) | $t_{max}$ (h) | AUC (pg * h/mL) | $t_{1/2}$ (h) | $C_{max}$/Dose | AUC/Dose |
|---|---|---|---|---|---|---|
| 3 | 15939.8 | 0.3 | 22365.9 | 0.2 | 613.1 | 860.2 |
| average | 23965.8 | 0.3 | 27191.2 | 0.5 | 921.8 | 1045.8 |
| min | 15939.8 | 0.3 | 22365.9 | 0.2 | 613.1 | 860.2 |
| max | 30655.7 | 0.3 | 35709.2 | 0.7 | 1179.1 | 1373.4 |
| SD | 7448.4 | 0.0 | 7398.5 | 0.3 | 286.5 | 284.6 |
| CV % | 31.1 | 0.0 | 27.2 | 54.7 | 31.1 | 27.2 |

TABLE 5

Stability data of the aqueous solution of Testosterone and HPβCD with a molar complexation ratio HPβCD:Tst 3:1

| | | 25° C. ± 2° C. /60% R.H. | | | | | | |
|---|---|---|---|---|---|---|---|---|
| Analysis | Specification | 0 | 3 m | 6 m | 9 m | 12 m | 18 m | 24 m |
| Testosterone Identification (HPLC) | Positive | Positive | Positive | Positive | Positive | Positive | Positive | Positive |
| Testosterone Assay | 95.0-105.0% of the theoretical value at release 90-105% of the theoretical value during stability study | 100.43 | 100.89 | 100.28 | 99.89 | 99.95 | 100.02 | 100.12 |
| Each individual unknown impurity | ≤0.2% | <0.1% | <0.1% | <0.1% | <0.1% | <0.1% | 0.1% | 0.1% |
| Total Impurities | ≤2.0% | 0.5% | 0.7% | 0.7% | 0.8% | 0.8% | 0.9% | 0.9% |
| TAMC | ≤100 CFU/g | <1 CFU/g | <1 CFU/g | <1 CFU/g | <1 CFU/g | <1 CFU/g | <1 CFU/g | <1 CFU/g |
| TYMC | ≤100 CFU/g | <1 CFU/g | <1 CFU/g | <1 CFU/g | <1 CFU/g | <1 CFU/g | <1 CFU/g | <1 CFU/g |
| Escherichia Coli | Absent/g | Absent/g | Absent/g | Absent/g | Absent/g | Absent/g | Absent/g | Absent/g |

Example 9—Comparative Pharmacokinetic Tests (Testosterone)

Figure 8:
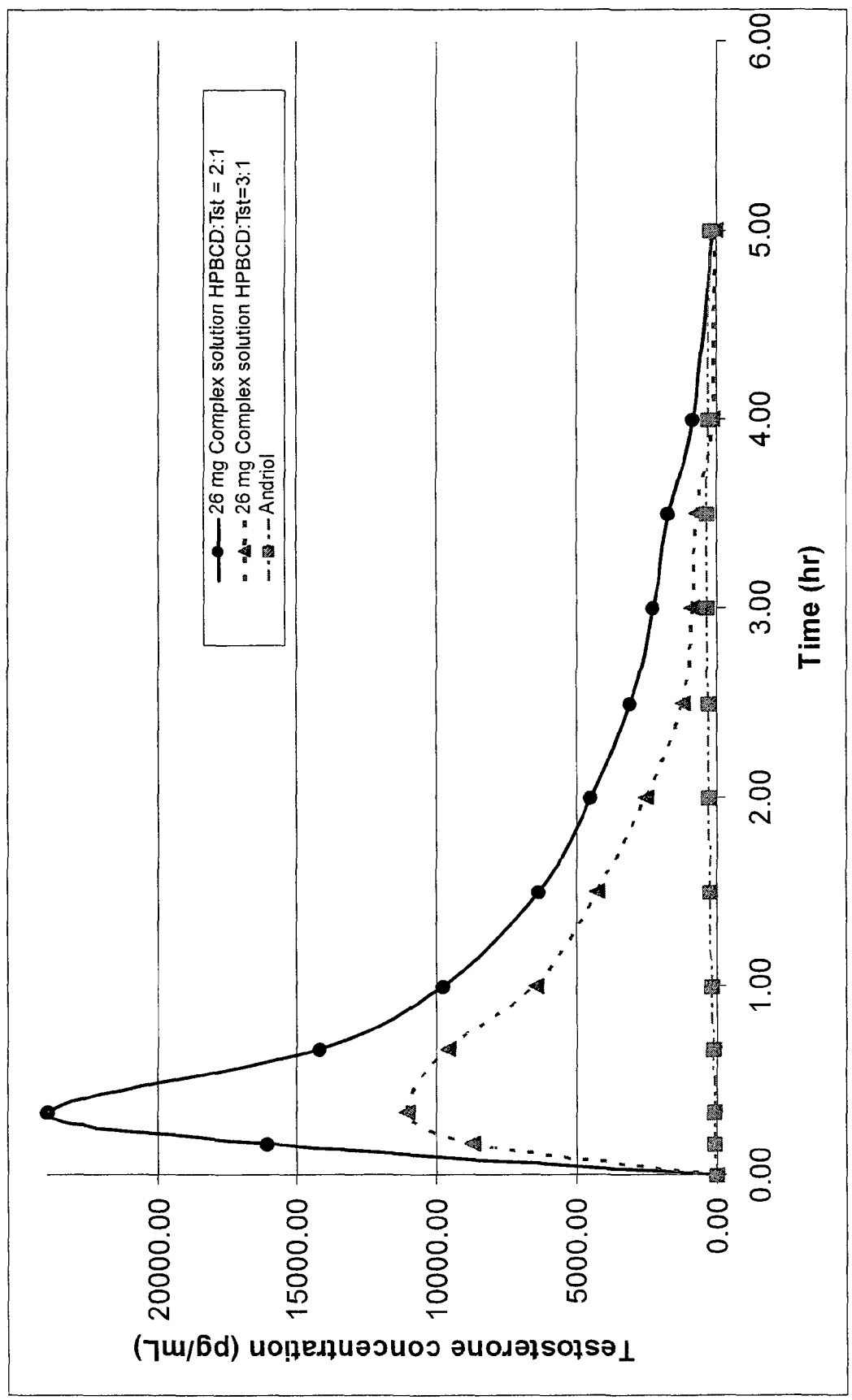
FIG. 8: Comparative plasma pharmacokinetic profiles of Testosterone in a healthy subject after oral administration of the solution of hydroxypropyl-β-cyclodextrin with Testosterone in a molar ratio 2:1 or 3:1, and of a Testosterone ester formulation present on the market (Andriol).

The solutions described in example 8 were used in a comparative clinical study of pharmacokinetics (FIG. 8 Tables 6-8). Three healthy female subjects, non or ex-smokers, with an age of between 18 and 75 years received, according to a crossover design, a single dose of 26 mg of Testosterone dissolved in the aforementioned solution or 40 mg of Testosterone undecanoate corresponding to 25.26 mg of Testosterone, in soft capsules (reference formulation on the market, Andriol). Tables 6-8 shows the results of the pharmacokinetics parameters obtained by the clinical study: Table 6 and 7 refer to the Testosterone formulations, object of the present patent, with respectively a molar ratio between HPβCD and Testosterone of 2:1 and 3:1, whereas Table 8 refers to the commercial reference formulation (Andriol).

TABLE 6

PK parameters of Testosterone administered as an oral solution completed with HPβCD, ratio 2:1

| Subject | $C_{max}$ (pg/mL) | $t_{max}$ (h) | AUC (pg * h/mL) | $t_{1/2}$ (h) | $C_{max}$/Dose | AUC/Dose |
|---|---|---|---|---|---|---|
| 1 | 30655.7 | 0.3 | 35709.2 | 0.7 | 1179.1 | 1373.4 |
| 2 | 25301.7 | 0.3 | 23498.6 | 0.6 | 973.1 | 903.8 |

TABLE 7

PK parameters of Testosterone administered as an oral solution complexed with HPβCD, ratio 3:1

| Subject | $C_{max}$ (pg/mL) | $t_{max}$ (h) | AUC (pg * h /mL) | $t_{1/2}$ (h) | $C_{max}$/Dose | AUC/Dose |
|---|---|---|---|---|---|---|
| 1 | 14185.4 | 0.3 | 19142.9 | 0.9 | 545.6 | 736.3 |
| 2 | 10021.3 | 0.3 | 16948.4 | 0.8 | 385.4 | 651.9 |
| 3 | 9015.7 | 0.3 | 14753.8 | 0.6 | 346.8 | 567.5 |
| average | 11074.1 | 0.3 | 16948.4 | 0.7 | 425.9 | 651.9 |
| min | 9015.7 | 0.3 | 14753.8 | 0.6 | 346.8 | 567.5 |
| max | 14185.4 | 0.3 | 19142.9 | 0.9 | 545.6 | 736.3 |
| SD | 2741.0 | 0.0 | 2194.5 | 0.1 | 105.4 | 84.4 |
| CV % | 24.8 | 0.0 | 12.9 | 18.1 | 24.8 | 12.9 |

TABLE 8

PK parameters of Testosterone, reference formulation (Andriol)

| Subject | Cmax (pg/mL) | tmax (h) | AUC (pg * h/mL) | t ½ (h) | Cmax/Dose | AUC/Dose |
|---|---|---|---|---|---|---|
| 1 | 225.6 | 3.5 | 886.0 | 1.3 | 8.9 | 35.1 |
| 2 | 453.7 | 3.5 | 3297.7 | 3.4 | 18.0 | 130.6 |
| 3 | 329.1 | 3.5 | 1789.2 | 2.3 | 13.0 | 70.8 |
| average | 336.1 | 3.5 | 1991.0 | 2.3 | 13.3 | 78.8 |
| min | 225.6 | 3.5 | 886.0 | 1.3 | 8.9 | 35.1 |
| max | 453.7 | 3.5 | 3297.7 | 3.4 | 18.0 | 130.6 |

TABLE 8-continued

PK parameters of Testosterone, reference formulation (Andriol)

| Subject | Cmax (pg/mL) | tmax (h) | AUC (pg * h/mL) | t ½ (h) | Cmax/Dose | AUC/Dose |
|---|---|---|---|---|---|---|
| SD | 114.2 | 0.0 | 1218.5 | 1.1 | 4.5 | 48.2 |
| CV % | 34.0 | 0.0 | 61.2 | 45.5 | 34.0 | 61.2 |

The results reported in Tables 6 and 7 show that the present composition generates an overall exposure per unit dose (AUC/dose) 13-fold ca. higher than that obtained with the Reference formulation (Table 8) in the case of a complex with molar ratio HPBCD:Tst 2:1 and of 8 times higher than that obtained with the Reference formulation (Table 8) in the case of a complex with molar ratio HPBCD:Tst 3:1. Similarly the peak concentrations per unit dose ($C_{max}$/Dose) are, for both complex solutions, higher than that obtained with the reference formulation. Moreover, the peak time ($t_{max}$) achieved with the HPBCD:Tst solutions is substantially lower as compared to that of the Reference formulation. The results confirm those obtained in Experiment 5 (FIGS. 5 and 6) and shown that the HPBCD:Tst complexes maintain a remarkable bioavailability despite being likely subject to the hepatic first-pass effect. A dose-effective treatment of Testosterone complexes with HPβCD via the oral route (more patient-friendly than e.g. complexes with HPβCD via the oral route (more patient-friendly than e.g. the sublingual/buccal/nasal route) is therefore obtained. As a further advantage, the composition of the invention makes it possible to significantly reduce the inter-individual variability of the plasma levels, expressed in the table by the CV % of AUC and $C_{max}$, with respect to the commercial formulation of Table 8.

The invention claimed is:

1. A method of treating a disease requiring Progesterone or Testosterone treatment, comprising orally administering to a patient in need thereof, a progesterone or testosterone complex of hydroxypropyl-β-cyclodextrin (HPβCD) in the form of a solution in which:
    said Progesterone (Prg) is present at a molar ratio HPβCD:Prg ranging from 1.7:1 to 2.4:1, or
    said Testosterone (Tst) is present at a molar ratio HPβCD:Tst ranging from 1.7:1 to 3.0:1;
    wherein said HPβCD contains less than 0.3% by weight of unsubstituted β-cyclodextrin, and
    wherein said Prg or Tst is present at a concentration ranging from 5 to 100 mg/g of said solution.

2. Method according to claim 1, wherein said molar ratio between the HPβCD and Prg or Tst ranges from 2.0:1 to 2.2:1.

3. Method according to claim 1, wherein said molar ratio between the HPβCD and Prg or Tst is about 2:1.

4. Method according to claim 1, wherein said complex is administered in the form of a ready-to-use solution, dispensed in a single-dose or multidose container made of glass or plastic material.

5. Method according to claim 1, wherein said solution is stable at room temperature for at least 24 months.

6. Method according to claim 1, wherein said Prg or Tst is present at a concentration ranging from 5 to 50 mg/g of solution.

7. Method according to claim 6, wherein said Prg or Tst is present at a concentration ranging from 15 to 40 mg/g of solution.

8. Method according to claim 1, wherein said molar ratio between the HPβCD and the Progesterone ranges from 1.9:1 to 2.1:1.

9. Method according to claim 1, wherein said molar ratio between the HPβCD and the Progesterone is about 2.1:1.

10. Method according to claim 1, wherein said molar ratio between the HPβCD and the Testosterone ranges from 1.9:1 to 2.1:1.

11. Method according to claim 1, wherein said molar ratio between the HPβCD and the Testosterone is about 2.1:1.

12. Method according to claim 1, wherein said solution is characterized by a higher transmembrane absorption of progesterone or testosterone compared to the corresponding solutions of progesterone or testosterone without said HPβCD.

13. Method according to claim 1, wherein said HPβCD is present in said progesterone solution at a minimal concentration of 27.0 mM or in said testosterone solution at a minimal concentration of 29.4 mM.

14. Method according to claim 1, wherein
    said solution is characterized by a higher transmembrane absorption of progesterone or testosterone compared to the corresponding solutions of progesterone or testosterone without said HPβCD, and
    said HPβCD is present in said progesterone solution at a minimal concentration of 27.0 mM or in said testosterone solution at a minimal concentration of 29.4 mM.

* * * * *